United States Patent [19]
Kuroiwa et al.

[11] Patent Number: 4,564,695
[45] Date of Patent: Jan. 14, 1986

[54] PROCESS FOR PRODUCING ARGINYL-P-NITROANILIDE

[75] Inventors: Katsumasa Kuroiwa; Shuichi Nakatsuyama, both of Koriyama; Takeshi Nagasawa, Urawa, all of Japan

[73] Assignee: Nitto Boseki Co., Ltd., Fukushimi, Japan

[21] Appl. No.: 650,353

[22] Filed: Sep. 13, 1984

[30] Foreign Application Priority Data

Sep. 14, 1983 [JP] Japan ............... 58-170402

[51] Int. Cl.$^4$ ............................. C07C 79/46
[52] U.S. Cl. ............................. 560/13; 560/22; 564/102; 564/138; 564/164; 564/194; 564/108
[58] Field of Search .............. 560/22, 13; 564/102, 564/138, 164, 194, 108

[56] References Cited

U.S. PATENT DOCUMENTS 4,016,042  4/1977  Svendsen ............ 195/103.5 R

OTHER PUBLICATIONS

Nishi et al., Bulletin of the Chemical Soc. of Japan, vol. 43, (1970), 2900–2907.
Somorin et al., Bull. Chem. Soc., Japan, vol. 51, (4) (1978) 1255–1256.

Primary Examiner—Bernard Helfin
Attorney, Agent, or Firm—Bert J. Lewen; Henry Sternberg

[57] ABSTRACT

An $N^\alpha$-protected-$N^G$-protected-arginyl-p-nitro-anilide with high purity can be produced in high yield by reacting an $N^\alpha$-protected-$N^G$-protected-arginine with p-nitroaniline in pyridine in the presence of a condensing agent.

4 Claims, No Drawings

PROCESS FOR PRODUCING ARGINYL-P-NITROANILIDE

This invention relates to a process for producing an $N^\alpha$-protected-$N^G$-protected-arginyl-p-nitroanilide.

Compounds represented by the formula:

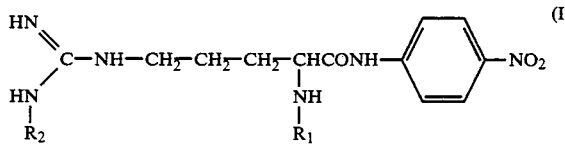

wherein $R_1$ is an α-amino protective group ($N^\alpha$-protective group) such as a carbobenzoxy group, a p-methoxycarbobenzoxy group, a t-butyloxycarbonyl group, a t-amyloxycarbonyl group, a trityl group, a p-nitrocarbobenzoxy group, a formyl group, a trifluoroacetyl group or the like; $R_2$ is an N-guanidino protective group ($N^G$-protective group) such as a nitro group, a tosyl group, a p-methoxybenzenesulfonyl group or the like or a hydrogen atom, and in the case of $R_2$ being a hydrogen atom, the N-guanidino group is protected by an acid such as hydrogen chloride, hydrogen bromide, p-toluenesulfonic acid or the like in the form of acid adduct, namely, $N^\alpha$-protected-$N^G$-protected-arginyl-p-nitroanilides are important as materials for producing arginyl-p-nitroanilide derivatives. The arginyl-p-nitroanilide derivatives (e.g., tosyl-arginyl-p-nitroanilide, tosyl-glycyl-prolyl-arginyl-p-nitroanilide, etc.) are, as well known, widely utilized for daily examination in the field of clinical examination as synthetic substrates used for measuring enzyme activities such as trypsin, thrombin, plasmin, kallikrein, urokinase, factor X and the like which are serine peptidases. When the enzyme acts on the arginyl-p-nitroanilide derivative, hydrolysis occurs so that p-nitroaniline is released, and the enzyme activity or the amount of enzyme can be known by measuring the UV absorption intensity of the p-nitroaniline released.

On a process for producing a compound of the formula (I), there are the following various reports:

(1) a process which comprises condensing carbobenzoxy-$N^G$-nitro-arginine with p-nitrophenyl isocyanate in hexamethylphosphoramide as a solvent (Bulletin of the Chemical Society of Japan, 43, 2900 (1970)), (2) a process which comprises condensing carbobenzoxy-$N^G$-nitro-arginine with p-nitroaniline in a dimethylformamide-tetrahydrofuran mixed solvent by using isobutyl chloroformate as an activator (U.S. Pat. No. 4,016,042.), (3) a process which comprises condensing carbobenzoxy-$N^G$-nitro-arginine with p-nitroaniline in dimethylformamide as a solvent by using dicyclohexylcarbodiimide as a condensing agent (U.S. Pat. No. 4,016,042), (4) a process which comprises condensing carbobenzoxy-arginine hydrochloride with p-nitrophenyl isocyanate in hexamethylphosphoramide as a solvent (U.S. Pat. No. 4,070,245), and (5) a process which comprises condensing carbobenzoxy-arginine with p-nitroaniline in ethyl phosphate as a solvent with heating by using phosphorus pentoxide as a condensing agent (Bulletin of the Chemical Society of Japan, 51(4), 1255 (1978)).

In the processes of (1) and (4), hexamethylphosphoramide is used as a solvent, but this solvent is carcinogenic and hence is unsuitable for using for industrial production processes. Further, p-nitrophenyl isocyanate is used for introducing p-nitroaniline, but this is economically disadvantageous as compared with processes in which p-nitroaniline is directly condensed.

On the other hand, in the processes of (2), (3) and (5), p-nitroaniline is directly introduced, but these processes are disadvantageous in that the yeild from reaction is low, that the amount of by-products is large, and that troublesome purification procedures such as chromatographic purification and the like are needed.

An object of this invention is to overcome the abovementioned problems and to provide a process for producing a compound of the formula (I) in high yield and high purity.

This invention provides a process for producing an $N^\alpha$-protected-$N^G$-protected-arginyl-p-nitroanilide represented by the formula:

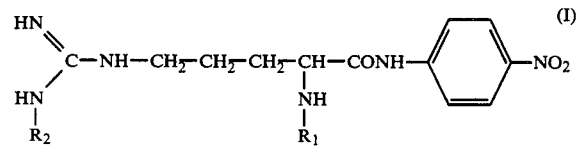

wherein $R_1$ is an α-amino ($N^\alpha$) protective group preferably selected from a carbobenzoxy group, a p-methoxycarbobenzoxy group, a t-butyloxycarbonyl group, a t-amyloxycarbonyl group, a trityl group, a p-nitrocarbobenzoxy group, a formyl group, a trifluoroacetyl group and the like; $R_2$ is an N-guanidino protective group preferably selected from a nitro group, a tosyl group, a p-methoxybenzenesulfonyl group and the like, or a hydrogen atom, and in the case of $R_2$ being a hydrogen atom, the N-guanidino group is preferably protected by an acid such as hydrogen chloride, hydrogen bromide or p-toluenesulfonic acid in the form of acid adduct, which comprises reacting an $N^\alpha$-protected-$N^G$-arginine of the formula:

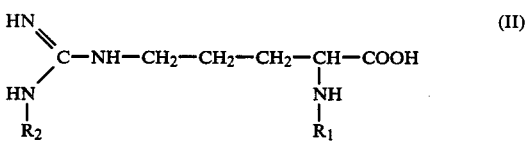

wherein $R_1$ and $R_2$ are as defined above, with p-nitroaniline in pyridine as a solvent in the presence of a condensing agent.

According to the process of this invention, the desired compound of the formula (I) can be obtained in high yield and good purity by a simple and economical means. The process of this invention cannot be suggested by the prior art at all. The reason for this is as follows. As shown by the above-mentioned results obtained by the conventional processes, the compound of the formula (II) is liable to undergo several side reactions in condensation with amino group, as known also in the case of peptide synthesis. When the amino group is p-nitroaniline, its amine activity is very low, so that side reactions occur particularly markedly. For these reasons, it has been thought very difficult to produce the desired compound of the formula (I) by condensation of a compound of the formula (II) with p-nitroaniline rapidly without any side reaction. However, the present inventors have found unexpectedly that a compound of the formula (II) can be subjected to dehydrating-condensation with p-nitroaniline in high convertion by use of pyridine as a solvent, whereby this invention has been accomplished.

As the $N^\alpha$-protected-$N^G$-protected-arginine of the formula (II), the following compounds can be used:

$N^\alpha$-carbobenzoxy-$N^G$-nitro-L-arginine, $N^\alpha$-t-butyloxycarbonyl-$N^G$-nitro-L-arginine, $N^\alpha$-carbobenzoxy-L-arginine.hydrochloride, $N^\alpha$-t-butyloxycarbonyl-L-arginine.hydrochloride, $N^\alpha$-t-butyloxycarbonyl-$N^G$-tosyl-L-arginine.

The compound of the formula (II) and p-nitroalinine are reacted with each other in about equivalent molar amounts.

The reaction is a dehydrating-condensation reaction and is carried out in pyridine as a solvent. If necessary, organic solvents such as dimethylformamide, tetrahydrofuran, dioxane, acetonitrile, ethyl acetate, chloroform and the like may be present in the reaction system preferably in a proportion of 10% or less.

The dehydrating-condensation reaction is carried out in the presence of a condensing agent. As the condensing agent, there can be used dialkylcarbodiimides (e.g., dicyclohexylcarbodiimide (DCCI)), water-soluble carbodiimides (e.g., N-ethyl-N'-3-dimethylamino-propyl-carbodiimide (WSCI), its hydrochloride), etc. The condensing agent is used preferably in an amount of equivalent mole to 30% by mole in excess per mole of the compound of the formula (II).

As to the reaction conditions, the reaction can be carried out by the conventional method for peptide synthesis using carbodiimide. For example, a condensing agent is added dropwise with cooling ($-10°$ C. to $5°$ C.), and after 1 to 3 hours, the reaction mixture is warmed and subjected to reaction at $10°-50°$ C., preferably $10°-30°$ C. for 1 to 24 hours. The condensing agent may be added in a solid state in small portions.

When a urethane type protective group such as a carbobenzoxy group, a methoxycarbobenzoxy group, a t-butyloxycarbonyl group, a t-amyloxycarbonyl group or the like is used as a protective group for the $\alpha$-amino group, the desired compound of the formula (I) can be obtained in high optical purity.

The protective groups can be removed by the methods conventionally used in peptide synthesis. Therefore, as a method for lengthening the peptide chain by removing the $N^\alpha$-protective group, a method for peptide synthesis can be used as it is.

As explained above, this invention has made it possible to produce an $N^\alpha$-protected-$N^G$-protected-argininyl-p-nitroanilide, which is a starting material for color-developable synthetic substrates, in high yield from inexpensive materials by a simple process.

This invention is further explained below in more detail referring to the following examples.

EXAMPLE 1

In 20 ml of anhydrous pyridine were dissolved 7.06 g (20 mmoles) of $N^\alpha$-carbobenzoxy-$N^G$-nitro-L-arginine and 2.76 g (20 mmoles) of p-nitroaniline. To the resulting solution was added dropwise, with stirring under ice-cooling, a solution obtained by dissolving 4.94 g (24 mmoles) of dicyclohexylcarbodiimide in 10 ml of anhydrous pyridine. After the resulting mixture was subjected to reaction overnight with stirring at room temperature, the dicyclohexylurea deposited was removed by filtration. The pyridine was removed by distillation under reduced pressure, after which 70 ml of ethyl acetate was added to the residue, and the resulting mixture was washed successively with 5% hydrochloric acid, a 10% aqueous sodium hydrogencarbonate solution and a saturated aqueous sodium chloride solution and dried over anhydrous sodium sulfate. The ethyl acetate was removed by distillation under reduced pressure, and the residue was recrystallized from n-butanol-methanol to obtain 8.0 g (84.6%) of crystals of $N^\alpha$-carbobenzoxy-$N^G$-nitro-L-arginyl-p-nitroanilide. Melting point: $186°-191°$ C. $[\alpha]_D^{20} -2.0°$(c=1, acetic acid).

The crystals gave a single spot ($R_f=0.74$) in a silica gel thin layer chromatography (chloroform:methanol:acetic acid:water=20:5:0.5:0.5).

Elementary analysis values: for $C_{20}H_{23}N_7O_7$: Found(%): C: 50.86, H: 4.90, N: 20.63. Calculated(%): C: 50.74, H: 4.90, N: 20.71.

EXAMPLE 2

In 60 ml of anhydrous pyridine were dissolved 9.57 g (30 mmoles) of $N^\alpha$-t-butyloxycarbonyl-$N^G$-nitro-L-arginine and 4.14 g (30 mmoles) of p-nitroaniline, and 6.89 g (36 mmoles) of N-ethyl-N'-3-dimethylaminopropylcarbodiimide (WSCI) hydrochloride was added with ice-cooling. The resulting mixture was subjected to reaction overnight at room temperature. The solvent was removed by distillation under reduced prossure, after which 200 ml of ethyl asetate was added to the residue, and the resulting mixture was washed successively with cold 5% hydrochloric acid, a 10% aqueous sodium hydrogen carbonate solution and a saturated aqueous sodium chloride solution and then dried over anhydrous magnesium sulfate. The solvent was removed by distillation under reduced pressure, and the residue was recrystallized from ethyl acetate-ether to obtain 9.8 g (74.4%) of crystals of $N^\alpha$-t-butyloxycarbonyl-$N^G$-nitro-L-arginyl-p-nitroanilide. Melting point: $199°-201°$ C. $[\alpha]_D^{20} -4.5°$(c=1, acetic acid).

The crystals gave a single spot ($R_f=0.74$) in a silica gel thin layer chromatography (chloroform:methanol:acetic acid:water=20:5:0.5:0.5).

Elementary analysis values: for $C_{17}H_{25}N_7O_7$: Found(%): C: 46.23, H: 5.73, N: 22.27. Calculated(%): C: 46.47, H: 5.73, N: 22.31.

REFERENTIAL EXAMPLE 1

To 5.4 g (12.3 mmole) of the $N^\alpha$-t-butyloxy-carbonyl-$N^G$-nitro-arginyl-p-nitroanilide was gradually dropped 84 ml of 3N HCl/AcOH, and the resulting mixture was subjected to reaction at room temperature for 1 hour and then poured into 840 ml of ether. After standing for 1 hour, the resulting precipitate was collected by filtration and dried overnight over phosphorus pentoxide and potassium hydroxide at $30°$ C. under reduced pressure. As a result, there was obtained 3.44 g (91.5%) of crystals of $N^G$-nitroarginyl-p-nitroanilide.hydrochloride which was a synthetic substrate. Melting point: $215°-218°$ C. $[\alpha]_D^{20} +62.5°$(c=0.2, methanol).

The crystals gave a single spot ($R_f=0.65$) in a silica gel thin layer chromatography (n-butanol:acetic acid:water=4:1:2).

Elementary analysis values: for $C_{12}H_{17}N_7O_5$.HCl: Found(%): C: 38.30, H: 5.01, N: 25.99. Calculated(%): C: 38.36, H: 4.83, N: 26.09.

EXAMPLE 3

In a mixed solvent of 24 ml of anhydrous pyridine and 6 ml of dimethylformamide were dissolved 6.89 g (20 mmoles) of $N^\alpha$-carbobenzoxy-L-arginine.hydrochloride and 2.76 g (20 mmoles) of p-nitroaniline, after which 4.94 g (24 mmoles) of dicyclohexylcarbodiimide was added in powder form, and the resulting mixture was subjected to reaction overnight with stirring at room temperature. The dicyclohexylurea deposited was removed by filtration, after which the solvent was removed by distillation under reduced pressure, and the residue was recrystallized from n-butanol-ethyl acetate to obtain 7.50 g (80.7%) of crystals of $N^\alpha$-carbobenzoxy-L-arginyl-p-nitroanilide.hydrochloride. Melting point: 181°–184° C. $[\alpha]_D^{20} - 11.0°(c=1,$ ethanol).

The crystals gave a single spot ($R_f$=0.50) in a silica gel thin layer chromatography (chloroform:methanol: acetic acid:water=20:5:0.5:0.5).

Elementary analysis values: for $C_{20}H_{24}N_6O_5 \cdot HCl$: Found(%): C: 51.71, H: 5.42, N: 17.85. Calculated(%): C: 51.67, H: 5.42, N: 18.08.

EXAMPLE 4

In 80 ml of anhydrous pyridine were dissolved 39.42 g (120 mmoles) of $N^\alpha$-t-butyloxycarbonyl-L-arginine.hydrochloride monohydrate and 16.56 g of p-nitroaniline, after which a solution of 49.44 g (240 mmoles) of dicyclohexylcarbodiimide in 60 ml of anhydrous pyridine was added dropwise to the resulting solution with ice-cooling, and the resulting mixture was subjected to reaction overnight with stirring at room temperature. The dicyclohexylurea deposited was removed by filtration, and the filtrate was concentrated under reduced pressure, after which the residue was dissolved in 400 ml of ethyl acetate, and the resulting solution was washed successively with a 2.8% aqueous ammonia (saturated with sodium chloride), a saturated aqueous sodium chloride solution and cold 5% hydrochloric acid (saturated with sodium chloride) and then dried over anhydrous magnesium sulfate. The solvent was removed by distillation under reduced pressure, and the residue was recrystallized from methanol-ethyl acetate to obtain 42.9 g (83.0%) of crystals of $N^\alpha$-t-butyloxycarbonyl-L-arginyl-p-nitroanilide hydrochloride. Melting point: 187°–190° C. $[\alpha]_D^{20} - 10°(c=1,$ methanol).

The crystals gave a single spot ($R_f$=0.5) in a silica gel thin layer chromatography (chloroform:methanol: acetic acid:water=20:5:0.5:0.5).

Elementary analysis values: for $C_{17}H_{26}N_6O_5 \cdot HCl$: Found(%): C: 47.16, H: 6.36, N: 19.39. Calculated(%): C: 47.39, H: 6.32, N: 19.50.

REFERENTIAL EXAMPLE 2

Arginyl-p-nitroanilide.dihydrochloride was produced by removing the $N^\alpha$-protective group from the $N^\alpha$-t-butyloxycarbonyl-L-arginyl-p-nitroanilide.hydrochloride obtained in Example 4.

In 45 ml of methanol was dissolved 15.0 g (34.8 mmoles) of the $N^\alpha$-t-butyloxycarbonyl-L-arginyl-p-nitroanilide. hydrochloride with heating, and 139.2 ml of 2N hydrochloric acid-acetic acid was gradually dropped to the resulting solution with stirring under ice-cooling. After completion of the dropping, the resulting mixture was stirred at room temperature for 1 hour (a part of crystals were deposited during the reaction), after which 210 ml of acetone was added, and the mixture thus obtained was allowed to stand overnight in a cold place. The precipitate was collected by filtration and dried under reduced pressure to obtain 10.9 g (86.3%) of crystals of arginyl-p-nitroanilide. dihydrochloride. Melting point: 240°–245° C. (decomp.). $[\alpha]_D^{20} - 76.5°(c=1,$ water).

The crystals gave a single spot ($R_f$=0.48) in a silica gel thin layer chromatography (n-butanol:acetic acid: water=4:1:2).

Elementary analysis values: for $C_{12}H_{18}N_6O_3 \cdot 2HCl$: Found(%): C: 39.36, H: 5.60, N: 22.70. Calculated(%): C: 39.25, H: 5.49, N: 22.88.

EXAMPLE 5

In 30 ml of anhydrous pyridine were dissolved 4.28 g (10 mmoles) of $N^\alpha$-t-butyloxycarbonyl-$N^G$-tosyl-arginine and 1.38 g (10 mmoles) of p-nitroaniline, after which a solution of 2.47 g (12 mmoles) of dicyclohexylcarbodiimide in 10 ml of anhydrous pyridine was added dropwise to the resulting solution with ice-cooling. After the addition, the resulting mixture was subjected to reaction overnight at room temperature.

The precipitate was removed by filtration, and the filtrate was concentrated under reduced pressure, after which 50 ml of ethyl acetate was added to the residue, and the resulting mixture was washed successively with cold 5% hydrochloric acid, 10% sodium hydrogencarbonate and a saturated aqueous sodium chloride solution and then dried over anhydrous magnesium sulfate. The solvent was removed by distillation under reduced pressure to obtained 5.2 g (94.9%) of oily $N^\alpha$-t-butyloxycarbonyl-$N^G$-tosyl-arginyl-p-nitroanilide. $[\alpha]_D^{20} + 2°(c=1$ methanol).

The oily substance gave a single spot ($R_f$=0.88) in a silica gel thin layer chromatography (chloroform: methanol:acetic acid:water=20:5:0.5:0.5).

Elementary analysis values: for $C_{24}H_{32}N_6O_7S_1$: Found(%): C: 52.60, H: 5.75, N: 15.10. Calculated(%): C: 52.54, H: 5.88, N: 15.32.

What is claimed is:

1. A process for producing an $N^\alpha$-protected-$N^G$-protected-arginyl-p-nitronilide of the formula:

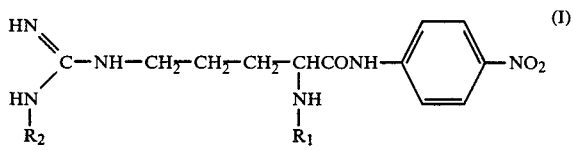

wherein $R_1$ is an α-amino protective group selected from the group consisting of a carbobenzoxy group, a p-methoxy-carbobenzoxy group, a t-butyloxycarbonyl group, a t-amyloxycarbonyl group, a trityl group, a p-nitrocarbobenzoxy group, a formyl group, and a trifluoroacetyl group; $R_2$ is an N-guanidino protective group selected from the group consisting of a nitro group, a tosyl group, and a p-methoxybenzenesulfonyl group or hydrogen, and in the case of $R_2$ being hydrogen, the N-guanidino group is protected by an acid in the form of a hydrochloride, hydrobromide or p-toluenesulfonate acid adduct, which comprises reacting an $N^\alpha$-protected-$N^G$-protected arginine of the formula:

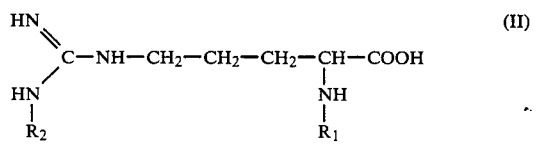

wherein $R_1$ and $R_2$ are as defined above, with p-nitroaniline in pyridine as a solvent in the presence of a dialkylcarbodiimide or a water-soluble carbodiimide condensing agent at a temperature of 10° to 50° C.

2. A process according to claim 1, wherein the condensing agent is dicyclohexycarbodiimide, or N-ethyl-N'-3-dimethylaminopropylcarbodiimide or hydrochloride thereof.

3. A process according to claim 1, wherein the reaction is carried out at room temperature.

4. A process according to claim 1, wherein the α-amino protective group is a carbobenzoxy group or a t-butyloxy carbonyl group.

* * * * *